(12) United States Patent
Roberts et al.

(10) Patent No.: US 11,724,066 B2
(45) Date of Patent: Aug. 15, 2023

(54) STRAIN RELIEF AND METHODS OF USE THEREOF

(71) Applicant: Cook Medical Technologies LLC, Bloomington, IN (US)

(72) Inventors: Erin Roberts, Bloomington, IN (US); Elizabeth M. Brown, Bloomington, IN (US); Jorge L. Jimenez-Rios, Bloomington, IN (US); Lyle Hundley, Bloomington, IN (US); Johnny P. Smith, Worthington, IN (US); Jonathan Sheets, Bloomington, IN (US); Jaimie Jarboe, Bloomington, IN (US); Nathan Steinbrunner, Bloomington, IN (US); Cayley Gubser, Bloomington, IN (US); Jeffry S. Melsheimer, Springville, IN (US); Samantha Charley, Ft. Wright, KY (US); Tyler Dow, Martinsville, IN (US); Kathryn R. Hardert, Bloomington, IN (US); David Gordon, Bloomington, IN (US); Kristen M. Bunch, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 351 days.

(21) Appl. No.: 17/026,557

(22) Filed: Sep. 21, 2020

(65) Prior Publication Data

US 2021/0085921 A1    Mar. 25, 2021

Related U.S. Application Data

(60) Provisional application No. 62/904,087, filed on Sep. 23, 2019.

(51) Int. Cl.
*A61M 25/00* (2006.01)
*A61M 25/01* (2006.01)

(52) U.S. Cl.
CPC .... *A61M 25/0053* (2013.01); *A61M 25/0097* (2013.01); *A61M 25/0136* (2013.01);
(Continued)

(58) Field of Classification Search
CPC .......... A61M 25/0097; A61M 25/0136; A61M 2025/0098; A61M 2205/02;
(Continued)

(56) References Cited

U.S. PATENT DOCUMENTS

| 4,427,033 A | 1/1984 | Ege |
| 5,143,409 A | 9/1992 | Lalikos |

(Continued)

FOREIGN PATENT DOCUMENTS

| GB | 2482058 A | 1/2012 |
| WO | 2015/050605 A1 | 4/2015 |
| WO | 2018/153661 | 8/2018 |

OTHER PUBLICATIONS

Strain Relief Fittings, Flexeel® & Flexcoil® Fittings, Coilhose Pneumatics, Nov. 5, 2018, http://coilhose.com/index.php/flexeel-and-flexcoil-fittings/strain-relief-fittings.html, 1 p.
(Continued)

*Primary Examiner* — Bhisma Mehta
*Assistant Examiner* — Phoebe Anne Staton
(74) *Attorney, Agent, or Firm* — Crowell & Moring LLP

(57) ABSTRACT

The present embodiments provide strain relief members for a medical device delivery system, methods of use thereof, and methods of manufacturing. In one embodiment a strain relief member may include a support having a first end with a first outer diameter, a second end having a second outer diameter, an inner surface facing a support lumen that
(Continued)

extends axially through the support along a longitudinal axis, and an outer surface opposite to the inner surface. An embodiment may also include an overlay coupled to a portion of the outer surface of the support, where the overlay comprises a first material and the support comprises a second material, and the first material is more flexible than the second material. A liner may be disposed in a portion of the support lumen and a first connector disposed over a portion of the support.

23 Claims, 4 Drawing Sheets

(52) U.S. Cl.
CPC ............... *A61M 2025/0047* (2013.01); *A61M 2025/0098* (2013.01); *A61M 2205/02* (2013.01); *A61M 2207/10* (2013.01)

(58) Field of Classification Search
CPC ...... A61M 25/0053; A61M 2025/0047; A61M 2207/10; A61M 25/0043; A61M 25/0014; A61M 39/1055; A61M 25/0054; A61M 25/005; A61B 2562/187; H01R 13/562
See application file for complete search history.

(56) References Cited

U.S. PATENT DOCUMENTS

| | | |
|---|---|---|
| 5,257,975 A | 11/1993 | Foshee |
| 5,358,493 A * | 10/1994 | Schweich, Jr. ... A61M 25/0054 604/525 |
| 6,068,622 A | 5/2000 | Sater et al. |
| 6,228,073 B1 | 5/2001 | Noone et al. |
| 7,837,157 B2 | 11/2010 | Linhart et al. |
| 7,985,205 B2 | 7/2011 | Adams |
| 8,807,489 B2 | 8/2014 | Su et al. |
| 9,017,308 B2 | 4/2015 | Klisch et al. |
| 9,326,789 B2 | 5/2016 | Fruland et al. |
| 9,675,486 B2 | 6/2017 | Jimenez, Jr. et al. |
| 9,989,187 B2 | 6/2018 | Siders et al. |
| 10,065,019 B2 | 9/2018 | Hamuro et al. |
| 2002/0169474 A1* | 11/2002 | Kusleika ................. A61F 2/013 606/200 |
| 2003/0040735 A1 | 2/2003 | Kunis et al. |
| 2006/0064159 A1* | 3/2006 | Porter ................. A61M 1/3655 623/1.24 |
| 2006/0252993 A1 | 11/2006 | Freed et al. |
| 2007/0156224 A1 | 7/2007 | Cionanta et al. |
| 2013/0153290 A1 | 6/2013 | Schlegel et al. |
| 2016/0346508 A1* | 12/2016 | Williams .......... A61M 25/0053 |
| 2018/0028783 A1 | 2/2018 | Dillon et al. |

OTHER PUBLICATIONS

C2312518, Cable gland M12x1.5, bending protection, OKW Gehäuse Systeme, 2 pp. Nov. 6, 2018.

Omegaflex® Coiled Polyurethane Hose with Strain Relief Fittings, omega.com, 2 pp., retrieved in Nov. 2019, as published online.

Cable Glands, Cable Glands & Adapters, NPT Threads Cable Glands, Mencom Corporation, U-4, 1 p., retrieved in Nov. 2019, as published online.

* cited by examiner

STRAIN RELIEF AND METHODS OF USE THEREOF

CROSS-REFERENCE TO RELATED APPLICATIONS

This application claims priority to U.S. Provisional Application Ser. No. 62/904,087, filed Sep. 23, 2019, which is incorporated herein by reference in its entirety.

TECHNICAL FIELD

This invention relates generally to medical devices, methods of use, and methods of manufacturing and more particularly, a strain relief member for a medical device delivery system.

BACKGROUND

When in use, a medical device may enter a patient at a convenient insertion location and then be urged to a target region. Once the distal portion of the medical device has entered the patient, a physician may urge the distal tip forward by applying longitudinal forces to the proximal portion of the medical device. To effectively communicate these longitudinal forces, it may be desirable for at least a portion of the device to have a level of pushability and kink resistance, particularly near the proximal end.

The path taken by a medical device within a patient may be tortuous, requiring the medical device to change direction frequently. In some cases, it may even be necessary for the medical device to double back on itself. Movement within a patient may also require precision. While advancing a medical device during a procedure, a physician may apply torsional forces to the proximal portion of the device to aid in steering the device. Torsional forces applied on the proximal end may translate to the distal end to aid in steering. It may be desirable, therefore, that the proximal portion of a medical device have a level of torqueablility to facilitate steering.

To facilitate manipulation of the proximal end of the medical device and/or to interface with ancillary devices, medical devices may include a proximal hub or manifold. Such a hub may include a port or connector for connecting the medical device to a handle or other device. In some devices, hubs may be adhesively bonded to the device along with a tubular strain relief. Due at least in part to the way that a medical device is held or used during a medical procedure, however, known strain reliefs may not be designed to sufficiently prevent the device from bending, kinking, or separation, leading to a loss of device function. An improved strain relief is needed to protect at least a portion of the proximal end of a medical device, for example, at a handle junction.

SUMMARY

The present disclosure provides a strain relief member for a medical device delivery system, methods of use thereof, and methods of manufacturing.

In one embodiment, a strain relief member for a medical device delivery system includes a support having a first end with a first outer diameter, a second end with a second outer diameter, an inner surface facing a support lumen that extends axially through the support along a longitudinal axis, and an outer surface opposite to the inner surface. An overlay is coupled to a portion of the outer surface of the support. The overlay includes a first material and the support includes a second material. The first material is more flexible than the second material. A liner is disposed in a portion of the support lumen. A first connector is disposed over a portion of the support.

In another embodiment, a strain relief member for a medical device delivery system includes a support having a first end with a first outer diameter, a second end with a second outer diameter, an inner surface facing a support lumen that extends axially through the support along a longitudinal axis, and an outer surface opposite to the inner surface. An overlay is coupled to a portion of the outer surface of the support. The overlay includes a first material and the support includes a second material. The first material is more flexible than the second material. A liner is disposed in a portion of the support lumen. A first connector is disposed over a portion of the support. A medical device shaft is disposed through the support lumen.

In a further embodiment, a method of manufacturing a strain relief member for a medical device delivery system includes forming a support having a first end with a first outer diameter, a second end having a second outer diameter, an inner surface facing a support lumen that extends axially through the support along a longitudinal axis, and an outer surface opposite to the inner surface. The method also includes coupling an overlay to a portion of the outer surface of the support. The overlay includes a first material and the support includes a second material. The first material is more flexible than the second material. The method further includes disposing a liner in a portion of the support lumen and disposing a first connector over a portion of the support.

Other systems, methods, features and advantages will be, or will become, apparent to one with skill in the art upon examination of the following figures and detailed description. It is intended that all such additional systems, methods, features and advantages be within the scope of the disclosure, and be encompassed by the following claims.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like referenced numerals designate corresponding parts throughout the different views. In certain instances, details may have been omitted that are not necessary for an understanding of aspects disclosed herein.

DETAILED DESCRIPTION

In the present application, the term "proximal" refers to a direction that is generally towards a physician during a medical procedure, while the term "distal" refers to a direction that is generally towards a target site within a patient's anatomy during a medical procedure. Reference to coupling or connection of components, unless specified otherwise, includes direct connection as well as connection through intervening components. In this disclosure, reference is made to a physician. Reference to a physician includes any other suitable medical practitioners. For example, physician assistants, nurses, or other health professionals.

In general and as described in more detail herein with reference to reference numbers and Figures, a medical device 2 for introducing a tool 4 into a patient is shown and described herein. Such a tool 4 may include a retrieval device. The device 2 may be implemented for use with tools 4 configured to extend to a remote location within a patient but may be further or alternatively implemented for other clinical, diagnostic, observational or other medical uses such as, deployment of structure, interacting with tissue in a remote location, observation, and the like.

Figure 9:
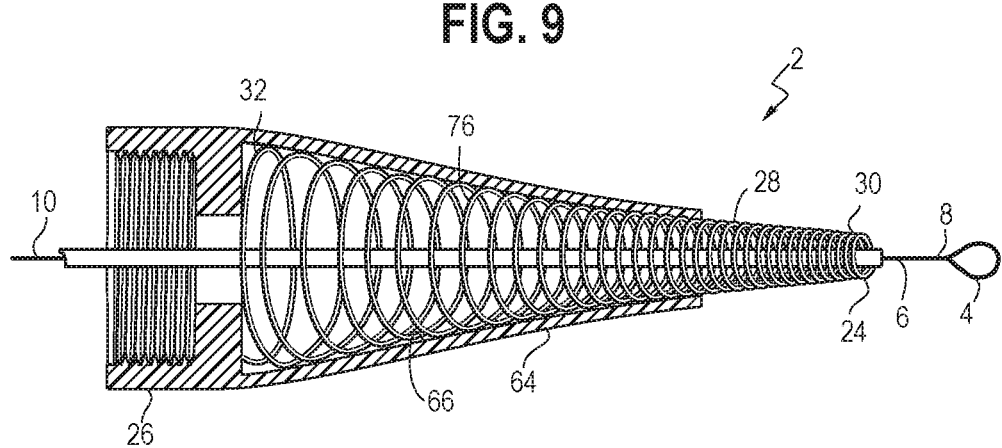
FIG. 9 is a perspective view of a seventh example of a strain relief member including a coil, a connector, and a tool.

In some embodiments, as shown in FIG. 9, the medical device 2 may include a medical device 2 shaft 6 with a tool 4 disposed at a distal end portion 8 of the medical device 2 shaft 6 and a handle 12 connected to a proximal end portion 10 of the medical device 2 shaft 6. In some embodiments, as shown in FIG. 9, a medical tool 4 is attached or otherwise coupled to a medical device 2 shaft 6. A medical device 2 shaft 6 may be solid or hollow. The handle 12 may be a medical device 2 handle 12. An inner surface 16 of the handle 12 may face a handle 12 lumen 20 (not shown). An outer surface 18 of the handle 12 is located opposite to the inner surface 16. The tool 4 may be a basket, such as a urology basket, while in other embodiments, the tool 4 may be a forceps, a snare, a loop, a laser fiber, an irrigation tube, the like, or any combination thereof. A tool 4 may include a variety of biocompatible materials and include a single material or a combination of materials, such as nitinol.

A strain relief 22 may be connected to the proximal end portion 10 of the medical device 2 shaft 6. A proximal portion 26 of the strain relief 22 may be coupled with the distal end portion 14 of the handle 12. A strain relief 22 may include a pliable design. In some embodiments, the strain relief 22 provides support to the proximal portion 10 of the medical device 2 shaft 6 and prevents at least a portion of the medical device 2 shaft 6 from bending or kinking. Some amount of bendability may be desired for flexibility, but unwanted bending could damage the medical device 2 shaft 6. A strain relief 22, therefore, may not be completely resistant to bending and a combination of elements and materials may be used to provide a sufficient balance between strength and flexibility for a particular medical device 2 or medical procedure. A strain relief 22 and components of a strain relief 22 may provide stiffness to protect a medical device 2 shaft 6 or catheter disposed at least partially within the strain relief 22 but allowing some flex. A strain relief 22 may additionally or alternatively prevent separation or damage at the junction of the medical device 2 shaft 6 and the handle 12.

In some embodiments, the proximal end portion 26 and the distal end portion 24 of a strain relief 22 may each have a circular cross section to accommodate the configuration of a medical device 2 shaft 6 that may be received within the strain relief 22. Additional configurations for the cross-sectional shape of the distal end and proximal end portions 24, 26 are possible including, but not limited to, oval, square, rectangular, triangular, and combinations thereof. The configuration (e.g., shape and dimension) of the cross sections of the distal end and proximal end portions 24, 26 may be varied as needed and/or desired, for example, to accommodate the configuration of various medical device 2 shafts 6, handles 12, and/or other medical devices.

Figure 2:
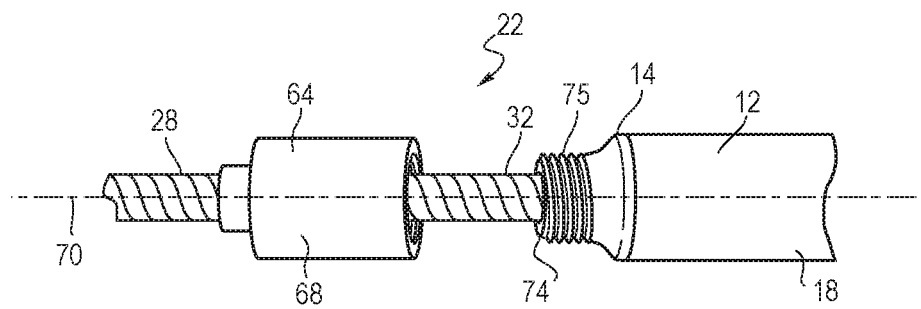
FIG. 2 is a perspective view of a second example of a strain relief member, where the strain relief member extends proximally into the distal end of a handle.

The strain relief 22 may include a support 28 extending between a proximal end portion 32 and a distal end portion 30. One end of a support 28 may be coupled to a handle 12. For example, the proximal portion 32 of a support 28 may be coupled to a distal end portion 14 of a handle 12. In some embodiments, a portion of the support 28 may be disposed over a portion of the outer surface 18 of the handle 12. In some embodiments, a portion of the support 28 is disposed in a portion of the handle 12 lumen 20. For example, as shown in FIG. 2, a support 28 may extend proximally into the distal end portion 14 of a handle 12.

The support 28 may include an inner surface 34 and an outer surface 36. The strain relief 22 may include a support 28 lumen 38 extending axially through the support 28 between the proximal end portion 32 and the distal end portion 30 along a longitudinal axis 70 (as shown in FIG. 2). An inner surface 34 of the support 28 may face a support 28 lumen 38. An outer surface 36 of the support 28 is located opposite to the inner surface 34. The support 28 lumen 38 may be open at the support's 28 distal and proximal ends 30, 32, for example for insertion of a medical device 2 shaft 6 and/or other components.

The length of a strain relief 22 may be about 5 centimeters to about 50 centimeters (e.g., from one end of a strain relief 22 to the other end of the strain relief 22). The length of a support 28 may be about 4 centimeters to about 15 centimeters (e.g., from one end of a support 28 to the other end of the support 28). The term "about" as used within the specification is specifically defined to include a range that includes the reference value as well as plus or minus 5 percent of the reference value. Dimensions of a strain relief 22 or support 28, however, may be on scale with the sizing and needs of the particular medical device 2, including for example medical device 2 components such as a handle 12, medical device 2 shaft 6, and tool 4. An inner diameter of a strain relief 22 may be sized to fit a medical device 2 shaft 6. In such an example, the inner diameter of a strain relief 22 is greater than the outer diameter of a medical device 2 shaft 6. An outer diameter of a strain relief 22 may be sized to fit within a first connector 64. In such an example, an outer diameter of a strain relief 22 is smaller than the inner diameter of a first connector 64.

Figure 1:
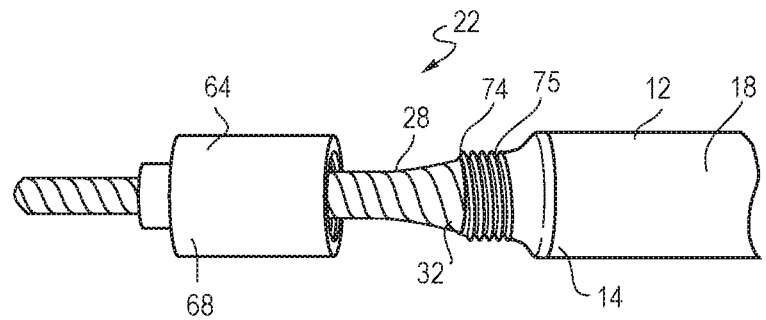
FIG. 1 is a perspective view of a first example of a strain relief member, where the strain relief member is coupled to the distal end of a handle.
Figure 4:
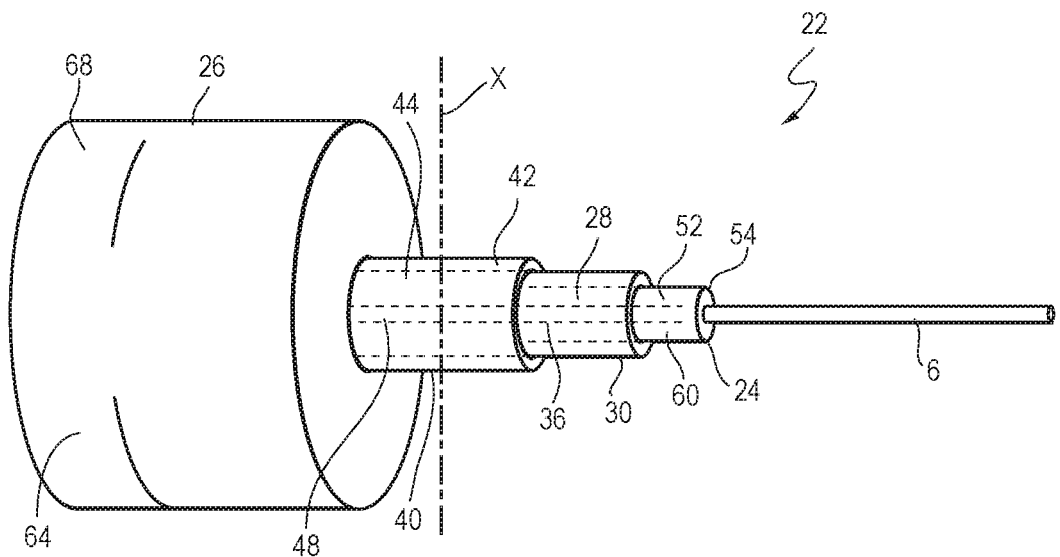
FIG. 4 is a perspective view of a fourth example of a strain relief member having at least three layers.

The support 28 may have a generally cylindrical or tubular shape with a substantially constant second outer diameter (e.g., FIG. 4). A support 28 may include a cannula, such as a laser-cut cannula. In some embodiments, however, the proximal end portion 32 of a support 28 may taper in a distal direction between the proximal end portion 32 and the distal end portion 30 from a first, relatively larger, outer diameter to a second, relatively smaller, outer diameter. For example, as shown in FIG. 1, the support 28 may have a funnel-shaped configuration near the proximal portion 32 of the support 28. In some embodiments, the support 28 may be conical, and may be a geometric conical profile with a constantly changing diameter along the length of the support 28. In other embodiments, the proximal end portion 32 may be shaped similar to a geometric cone (i.e. with a decreasing diameter along its length) but the rate of change of diameter may not be constant, such that a cross-section of the proximal end portion 32 forms a curve. The proximal end portion 32 may alternatively taper in a proximal direction between the proximal end portion 32 and the distal end portion 30 from a first, relatively larger, outer diameter to a second, relatively smaller, outer diameter. In some embodiments, a support 28 may include a coil 76, a spring, a braid, a weave, or any combination thereof.

Figure 6:
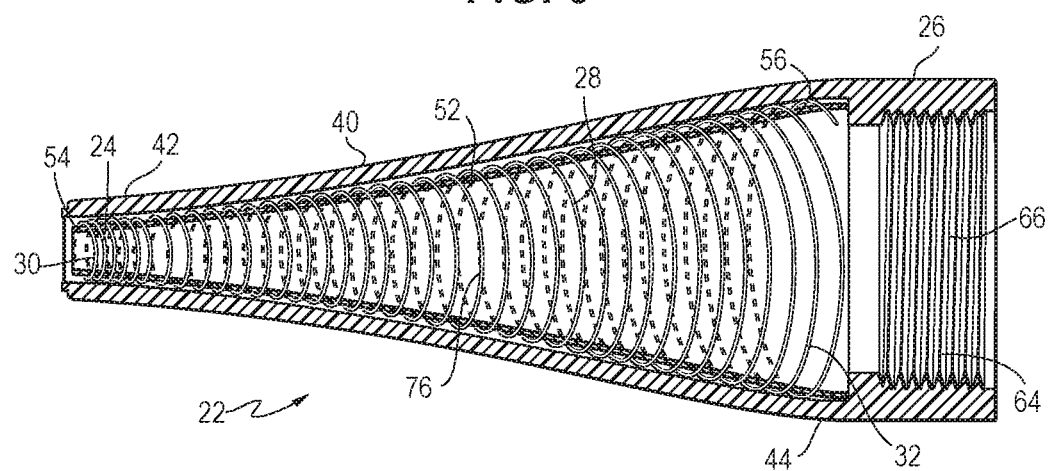
FIG. 6 is a perspective view of a fifth example of a strain relief member including a coil and a connector.
Figure 7:
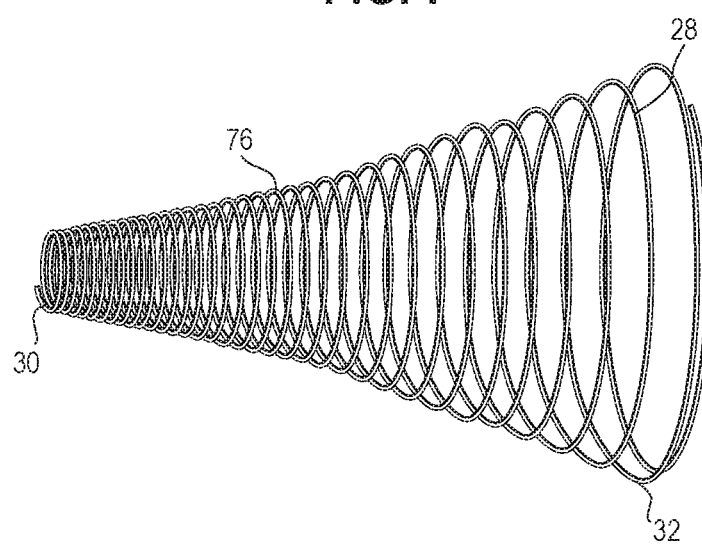
FIG. 7 is a perspective view of a strain relief member coil component.
Figure 8:
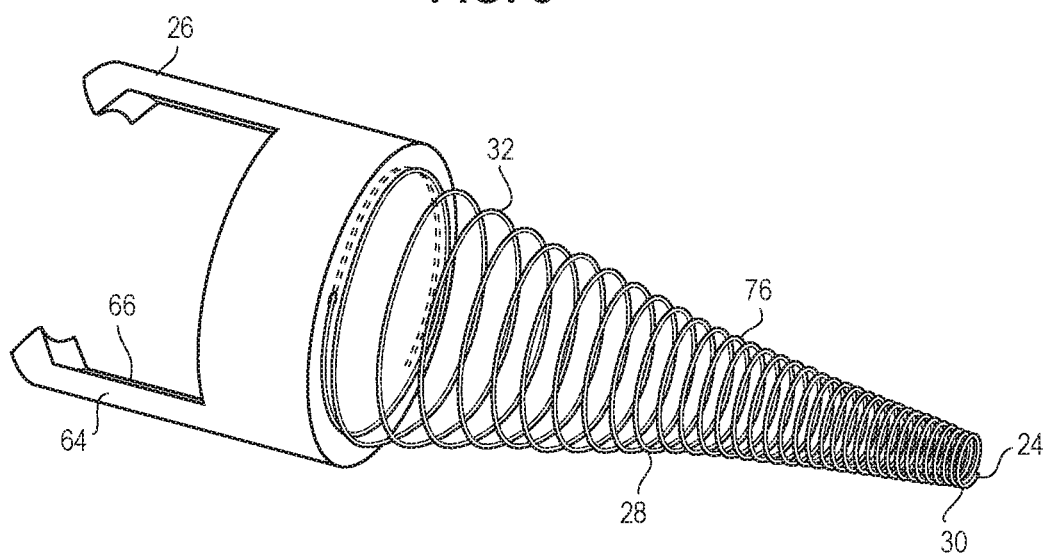
FIG. 8 is a perspective view of a sixth example of a strain relief member including a coil and a connector.

FIGS. 3, 6, and 7-9 show examples where a support 28 includes a coil 76. When a support 28 includes a coil 76, the coil 76 may include a variety of materials as described for a support 28, including a metal such as stainless steel or nitinol. In some embodiments, a coil 76 assists with flexibility as well as reinforcement against unwanted bending or separation at a handle 12 junction or other connection point. The strain relief 22 of FIG. 6 includes a coil 76 coupled to a first connector 64. The inner surface 66 of the first connector 64 in FIG. 6 is threaded. FIG. 7 demonstrates an example funnel coil shape 76 that may be used for a support 28. In FIG. 7, a coil 76 is flared and continues to tighten extending along the coil 76 in a distal direction while becoming more spaced apart. FIG. 8 demonstrates a coil 76 with a consistent diameter along its length and coupled to a first connector 64.

Figure 3:
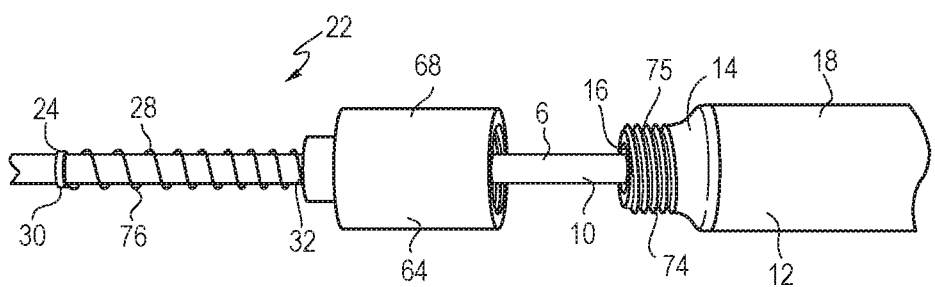
FIG. 3 is a perspective view of a third example of a strain relief member, where the strain relief member includes a coil.

In some embodiments, as shown in FIG. 3, a support 28 includes a coil 76 with a variable pitch. In FIG. 3, a coil 76 is coupled to a first connector 64. The coil 76 extends distally away from the first connector 64 varying from a tighter spacing to a more loose spacing. A coil 76 may be tightly or loosely wound around a medical device 2 shaft 6. In an embodiment including a coil 76, an overlay 40 may be disposed over the coil 76 and a liner 52 disposed under the coil 76. FIG. 9 demonstrates a coil 76 where the first connector 64 is disposed over the outer surface 36 of the coil 76. As shown in FIG. 9, a first connector 64 may be disposed over a portion of a support 28, with the support 28 extending distally out of an opening in the first connector 64.

The support 28 may include a first end with a first outer diameter and a second end with a second outer diameter. The value of a first outer diameter may be different than the value of the second outer diameter. In some embodiments, one of the distal or proximal ends 30, 32 has a first outer diameter and the other one of the distal or proximal end 30, 32 has a second outer diameter. Alternatively, the value of a first outer diameter may be the same or about the same as the value of the second outer diameter. The support 28 lumen 38 may be a suitable diameter for a medical procedure, for example, about 1.0 French to about 4.5 French. The outer diameter of the support 28 may be greater than the diameter of the support 28 lumen 38, ranging from about 1.5 French to about 25 French. For a tapered support 28, the largest diameter may be approximately 0.40 inches/10 millimeters and taper down to a diameter larger than the outer diameter of component(s) disposed within the support 28 lumen 38, such as a medical device 2 shaft 6 and/or a liner 52. The lumen 38 may have a consistent diameter throughout the support 28, regardless of whether the outer surface 36 of the support 28 is tapered or otherwise shaped.

The support 28 lumen 38 may be a tubular shape having a constant diameter. In some embodiments, however, as shown in FIG. 1, the support 28 lumen 38 may also or alternatively taper in a distal direction between the proximal end portion 32 and the distal end portion 30 from a first, relatively larger, diameter to a second, relatively smaller, diameter. In some embodiments, the lumen 38 may be conical, and may be a geometric conical profile with a constantly changing diameter along the length of the support 28. In other embodiments, the lumen 38 may be shaped similar to a geometric cone (i.e. with a decreasing diameter along its length) but the rate of change of diameter may not be constant, such that a cross-section of the lumen 38 forms a curve. The lumen 38 may alternatively taper in a proximal direction between the proximal end portion 32 and the distal end portion 30 from a first, relatively larger, outer diameter to a second, relatively smaller, outer diameter. The shape and size of a support 28 lumen 38 may mimic the shape and/or size of a support's 28 outer surface 36 and/or diameter(s) but where the support 28 lumen 38 is scaled down in comparison in order to fit within the support 28.

In some embodiments, one or multiple structures extend through and/or are disposed within the support 28 lumen 38. As discussed above, a medical device 2 shaft 6 may extend through the support 28 lumen 38. A liner 52 may be disposed in a portion of the support 28 lumen 38. A liner 52 may extend through the support 28 lumen 38, for example, between an inner surface 34 of the support 28 and a medical device 2 shaft 6. An inner surface 58 of the liner 52 may face a liner 52 lumen 62. An outer surface 60 of the liner 52 is located opposite to the inner surface 58. A liner 52 may extend over at least a portion of the surface of the medical device 2 shaft 6. A liner 52 may be adhered or otherwise coupled to the inner surface 34 of the support 28. A liner 52 may include a material with a lubricous region.

In some embodiments, one or multiple structures extend around at least a portion of the support 28, for example, around a portion of the outer surface 36 of the support 28. An overlay 40 may be disposed over or otherwise coupled to at least a portion of the outer surface 36 of the support 28. An inner surface 46 of the overlay 40 may face an overlay 40 lumen 50. An outer surface 48 of the overlay 40 is located opposite to the inner surface 46. In some embodiments, the addition of an overlay 40 to a strain relief 22 may be referred to as a lamination and placement of an overlay 40 as a laminating step.

In some embodiments, an overlay 40 includes a first material and the support 28 includes a second material where the first material is more flexible than the second material. In some embodiments, the support 28 may be made from a soft to semi-rigid material or a rigid material. Example support 28 materials include a metal, stainless steel, nitinol, a plastic, polycarbonate, acrylonitrile butadiene styrene, PEBAX, polyurethane, like biocompatible materials, or any combination thereof. In some embodiments, the overlay 40 may be made from a soft to semi-rigid material such as a plastic, polyurethane, PEBAX, polyethylene, polypropylene, fluorocarbon polymers, silicone, latex, polyvinyl chloride, polyether block amide, cope loop tubing, like biocompatible polymeric materials, or any combination thereof. In some examples, an overlay 40 may be referred to as an outer polymer or a soft polymer. Any suitable material may be used to form the overlay 40 such that the overlay 40 is sufficiently flexible to facilitate maneuvering a tool 4 disposed inside a patient's body, but also has enough strength to provide support and prevent kinking or separation. A liner 52 may include a material that is more lubricous than an overlay 40 material or support 28 material. Example liner 52 materials include polyimide, polytetrafluoroethylene, like biocompatible materials, or any combination thereof.

A strain relief 22 may additionally or alternatively include internal reinforcement, such as a nitinol cannula. Such internal reinforcement may contribute to prevention of kinking and separation from a handle 12 junction. Internal reinforcement may be disposed between the inner surface 34 of the support 28 and the outer surface 60 of the liner 52. Internal reinforcement may be disposed between the inner surface 58 of the liner 52 and a medical device 2 shaft 6. Internal reinforcement may be disposed between the inner surface 46 of the overlay 40 and the outer surface 36 of the support 28.

As shown in FIG. 4, a first connector 64 may be disposed at the proximal end portion 26 of the strain relief 22. In some embodiments, a first connector 64 secures at least a portion of the strain relief 22. The first connector 64 includes an inner surface 66 and an outer surface 68. The first connector 64 may be threaded, for example, where threads are located on the first connector's 64 inner surface 66. An inner diameter of a first connector 64 may be about 0.3 millimeters to about 2.0 millimeters. For example, in one embodiment, an inner diameter of a first connector 64 may be about 1.75 millimeters. The first connector 64 may be a female luer connector or a male luer connector. In some embodiments, at least a portion of the first connector 64 covers at least a portion of an overlay 40, a support 28, and/or a liner 52. A first connector 64 may be disposed over a portion of the support 28, such as a region of the outer surface 36 of the support 28. A first connector 64 may additionally or alternatively be disposed over a portion of an overlay 40, such as a region of the outer surface 48 of an overlay 40. A first connector 64 may be additionally or alternatively disposed over a portion of a liner 52, such as a region of the outer surface 60 of a liner 52. In some embodiments, only a portion of the inner surface 66 of the first connector 64 may be disposed over a component (such an overlay 40, a support 28, and/or a liner 52). For example, as shown in FIG. 9, a portion of the inner surface 66 of the first connector 64, such as a threaded portion, may be disposed adjacent to the proximal end portion of an overlay 40, a support 28, and/or a liner 52 (44, 32, 56, respectively). A medical device 2 shaft 6 may extend proximally past a proximal end of an overlay 40, a support 28, and/or a liner 52 (44, 32, 56, respectively), as shown in FIG. 9.

Figure 5:
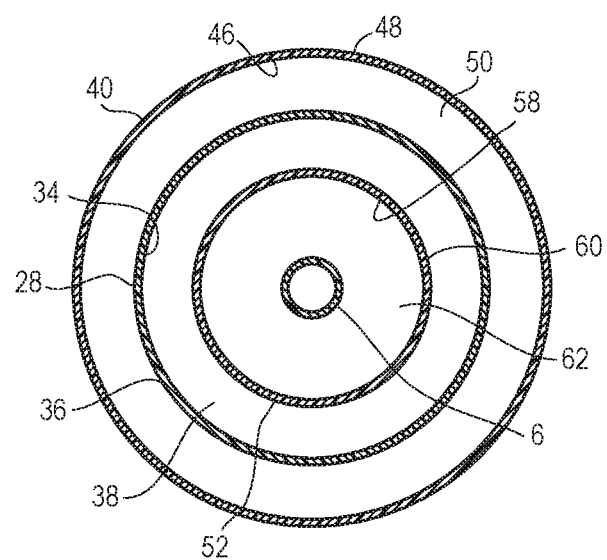
FIG. 5 is a sectional view of cross section 'X' of the strain relief member of FIG. 4.

In FIG. 4, a first connector 64 is disposed over the combination of the overlay 40, support 28, and liner 52. A medical device 2 shaft 6 extends distally through the combination. The first connector 64 may be coupled to a second connector 74 and/or a handle 12. In this example, the strain relief 22 protects the medical device 2 shaft 6 from unwanted bending or kinking. The combination of an overlay 40, support 28, and liner 52 may be a layered polymer embodiment where each polymer layer provides increasing rigidity and/or hardness, for example, as measured by a durometer. For example, a liner 52 may include a polymer having a first rigidity, a support may include a polymer having a second rigidity greater than the first rigidity, and an overlay 40 may include a polymer having a third rigidity greater than the second rigidity. Such an embodiment may be layered, for example, as shown in FIGS. 4 and 5.

The overlay 40, support 28, and liner 52 of FIG. 4 are arranged stepwise, for example, with the liner 52 extending furthest distally and the overlay 40 extending the least furthest distally and the support 28 extending distally to a location in between. In some embodiments, however, the distal end portions of the overlay 40, support 28, and liner 52 (42, 30, 54 respectively) are disposed at the same or about the same location. FIG. 5 is a cross-sectional view along the 'X' indicated in FIG. 4. As shown in FIG. 5, for example, the overlay 40, support 28, and liner 52 may be coaxial. A longitudinal axis 70 may be the common axis of an overlay 40, support 28, and liner 52. FIG. 5 demonstrates a view of an example combination of an overlay 40, a support 28, and a liner 52 disposed coaxially and having a medical device 2 shaft 6 disposed along the longitudinal axis 70.

FIG. 1 shows a combination of a handle 12, first connector 64, second connector 74, and support 28. The support 28 of FIG. 1 may include an overlay 40 over at least a portion of the outer surface 36 of the support 28 and a liner 52 coupled to at least a portion of the inner surface 34 of the support 28. A medical device 2 shaft 6 may be disposed through the support 28, the first connector 64, the second connector 74, and at least a portion of the handle 12. The inner surface 66 of the first connector 64 is threaded and complementary to the outer surface 75 of the second connector 74. In FIG. 1, the support 28 extends through the length of the first connector 64. In some examples, a strain relief 22 component includes a proximal flared end that abuts a distal end 14 of a handle 12. As shown in FIG. 1, the proximal portion 32 of a support 28 flares out at a handle 12 junction at the handle's 12 distal end 14. A support 28 may be disposed at least partially over the outer surface 18 of a handle 12 and/or an outer surface 75 of a second connector 74. However, in some embodiments, a support 28 may merely abut the distal end portion 14 of the handle 12. The first connector 64 may be slid proximally down the support 28 and coupled to the handle 12 via coupling of the first connector 64 to the second connector 74. FIG. 2 shows an alternative embodiment, where the proximal portion 32 of the support 28 does not flare out at the handle 12 junction. In FIG. 2, the support 28 extends at least partially into the handle 12. In some embodiments, however, a support 28 may merely abut the distal end portion 14 of the handle 12.

Any suitable connecting means may be used to couple the strain relief 22 to the handle 12. For example, as shown in FIGS. 1-3, a medical device 2 may also include a second connector 74. A component extending through the first connector 64 for example a medical device 2 shaft 6, overlay 40, support 28, and/or liner 52, may also extend through or into the second connector 74. The second connector 74 may be coupled to the first connector 64. The second connector 74 may be complementary to the first connector 64 such that the first connector 64 and the second connector 74 may be coupled together. For example, the first connector 64 may be a threaded female luer connector and the second connector 74 may be a threaded male luer connector. In the example with the threaded female and male luer connectors, the connectors may be screwed together to couple (e.g., FIGS. 1-3). Alternative forms of connection may be suitable for some embodiments, for example, a snap connection. A second connector 74 may be coupled to a handle 12 or formed integrally with a handle 12.

The first and/or second connector 64, 74 may each be made from a material less flexible than the material used to make the overlay 40. In some embodiments, a connector 64, 74 may be made from a semi-rigid to rigid plastic material such as a plastic, acrylonitrile butadiene styrene, like biocompatible materials, or any combination thereof.

In some embodiments, a component of the strain relief 22 may be extruded, or injection molded, laser cut, or over molded. All components may be made using the same process. In alternative embodiments, a portion of the strain relief 22 is extruded, injection molded, or over molded while other portion(s) of the strain relief 22 are made using a different process. A method of manufacturing a strain relief 22 for a medical device 2 delivery system may include, in any order, forming a support 28, coupling an overlay 40 to a portion of the support's 28 outer surface 36, disposing a liner 52 in a portion of the support 28 lumen 38, and disposing a first connector 64 over a portion of the support 28.

Before using a strain relief 22 to direct a tool 4 of the medical device 2 shaft 6 into a patient, in some embodiments, the strain relief 22 may be already provided on and stored with the medical device 2 shaft 6, such that the strain relief 22 is in readiness for use by a physician. In some embodiments, the strain relief 22 may be stored separately from the medical device 2 and thus a physician places the strain relief 22 onto the medical device 2 shaft 6 of the medical device 2 prior to use. To prep the strain relief 22 for use, the physician may thread either the distal end or proximal end 24, 26 of the strain relief 22 onto a medical device 2 shaft 6.

A user may place the tool 4 inside a patient's body (which may be inserted with or without the use of a guide wire) such that the medical device 2 shaft 6 may be used to direct the tool 4 to the desired location where an object to be extracted, or a clinical area to be investigated, observed, or interacted with is located. For example, a user may place a ureteral stone extractor 4 inside a patient's body such that the medical device 2 shaft 6 may be used to direct the extractor 4 to a desired location. The user may manipulate the medical device 2 to perform a medical procedure without unnecessary medical device 2 shaft 6 kinking or damage to a junction between the medical device 2 shaft 6 and a handle 12.

After use, the user may decouple the strain relief 22 from a medical device 2 such that the strain relief 22 may again be used for a subsequent procedure. The user may also remove (e.g., by peeling off) the strain relief 22 from the medical device 2 shaft 6 as needed or desired. In some embodiments, the strain relief 22 may be configured to be peeled away from the medical device 2 shaft 6, for example, for disposal. The strain relief 22 may include a slit or spiral cut on an overlay 40, a support 28, and/or a liner 52 such that the strain relief 22 may be removed from the medical device 2 after the strain relief 22 has been used to direct a distal end 8 of the medical device 2 shaft 6 to a desired location. Alternatively, the strain relief 22 may be disposed of subsequent to a procedure along with the medical device 2, functioning as a one-time-use device.

While various embodiments are described herein, the disclosure is not to be restricted except in light of the attached claims and equivalents. One skilled in the relevant art will recognize that numerous variations and modifications may be made to the embodiments described above. Moreover, the advantages described herein are not necessarily the only advantages and it is not necessarily expected that every embodiment will achieve all of the advantages described.

We claim:

1. A strain relief member for a medical device delivery system, comprising:
    a support comprising a first end comprising a first outer diameter, a second end comprising a second outer diameter, an inner surface facing a support lumen that extends axially through the support along a longitudinal axis, and an outer surface opposite to the inner surface;
    an overlay coupled to a portion of the outer surface of the support,
    wherein the overlay comprises a first material and the support comprises a second material, and the first material is more flexible than the second material;
    a liner disposed in a portion of the support lumen; and
    a first connector disposed over a portion of the support;
    wherein the liner comprises a first polymer comprising a first rigidity, the support comprises a second polymer with a second rigidity greater than the first rigidity, and the overlay comprises a third polymer with a third rigidity greater than the second rigidity.

2. The strain relief member of claim 1, wherein the first connector is disposed over a portion of the overlay.

3. The strain relief member of claim 1, wherein the first connector is disposed over a portion of the liner.

4. The strain relief member of claim 1, wherein the support comprises a coil, a braid, a weave, or any combination thereof.

5. The strain relief member of claim 1, wherein the support comprises a variable pitch coil.

6. The strain relief member of claim 1, wherein the support comprises a length of about 4 centimeters to about 15 centimeters from the first end of the support to the second end of the support.

7. The strain relief member of claim 1, wherein the first connector is threaded, is a female luer connector, or is a male luer connector.

8. The strain relief member of claim 1, wherein the first outer diameter is larger than the second outer diameter.

9. The strain relief member of claim 1, further comprising a handle, wherein the first end of the support is coupled to the handle.

10. The strain relief member of claim 9, wherein the handle further comprises a handle inner surface and a handle outer surface opposite to the handle inner surface.

11. The strain relief member of claim 10, wherein a part of the support is disposed over a portion of the handle outer surface.

12. The strain relief member of claim 10, wherein the handle further comprises a handle lumen facing the handle inner surface, wherein a part of the support is disposed in a portion of the handle lumen.

13. The strain relief member of claim 1, wherein the liner comprises polyimide, polytetrafluoroethylene, a material with a lubricious region, or any combination thereof.

14. The strain relief member of claim 1, wherein the support lumen comprises a diameter of about 1.0 French to about 4.5 French.

15. The strain relief member of claim 1, wherein the first material comprises polyurethane, silicone, latex, polyvinyl chloride, polyether block amide, polyethylene, polypropylene, fluorocarbon polymers, cope loop tubing, or any combination thereof.

16. The strain relief member of claim 1, wherein the second material comprises stainless steel, nitinol, a plastic, polycarbonate, acrylonitrile butadiene styrene, polyether block amide, polyurethane, or any combination thereof.

17. A strain relief member for a medical device delivery system, comprising:
    a handle;
    a support comprising a first end comprising a first outer diameter, a second end comprising a second outer diameter, an inner surface facing a support lumen that extends axially through the support along a longitudinal axis, and an outer surface opposite to the inner surface;
    an overlay coupled to a portion of the outer surface of the support, wherein the overlay comprises a first material and the support comprises a second material, and the first material is more flexible than the second material;
a liner disposed in a portion of the support lumen;
a first connector disposed over a portion of the support; and
a medical device shaft through the support lumen;
wherein the handle further comprises a handle lumen and wherein the support is disposed in a portion of the handle lumen.

18. The strain relief member of claim 17, wherein the first end of the support is coupled to the handle.

19. The strain relief member of claim 17, wherein the handle further comprises a handle inner surface facing the handle lumen, and a handle outer surface opposite to the handle inner surface, wherein a portion of the support is disposed over a portion of the handle outer surface.

20. The strain relief member of claim 19, further comprising a second connector, wherein the second connector is coupled to the first connector.

21. The strain relief member of claim 20, wherein the second connector is complementary to the first connector.

22. The strain relief member of claim 17, further comprising a medical tool attached to the medical device shaft.

23. The strain relief member of claim 22, wherein the medical tool is a basket.

* * * * *